(12) United States Patent
Kalgutkar et al.

(10) Patent No.: US 7,732,633 B2
(45) Date of Patent: *Jun. 8, 2010

(54) ARYLSULFINATE SALTS IN PHOTOINITIATOR SYSTEMS FOR POLYMERIZATION REACTIONS

(75) Inventors: Rajdeep S. Kalgutkar, St. Paul, MN (US); Michael C. Palazzotto, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/428,634

(22) Filed: Apr. 23, 2009

(65) Prior Publication Data

US 2009/0203904 A1 Aug. 13, 2009

Related U.S. Application Data

(62) Division of application No. 11/380,028, filed on Apr. 25, 2006, now Pat. No. 7,541,389, which is a division of application No. 10/847,523, filed on May 17, 2004, now Pat. No. 7,064,152.

(60) Provisional application No. 60/506,396, filed on Sep. 26, 2003.

(51) Int. Cl.
C07C 313/00 (2006.01)
(52) U.S. Cl. .......................... 562/125; 562/126
(58) Field of Classification Search .................. 562/30, 562/125, 126
See application file for complete search history.

(56) References Cited

U.S. PATENT DOCUMENTS

| | | | |
|---|---|---|---|
| 3,556,794 A | 1/1971 | Margerum | |
| 3,573,922 A | 4/1971 | Rust | |
| 3,607,272 A | 9/1971 | Rust | |
| 3,623,875 A | 11/1971 | Desjarlais et al. | |
| 3,627,656 A | 12/1971 | Miller et al. | |
| 3,642,487 A | 2/1972 | Rust | |
| 3,708,296 A | 1/1973 | Schlesinger | |
| 3,729,313 A | 4/1973 | Smith | |
| 3,741,769 A | 6/1973 | Smith | |
| 3,788,858 A | 1/1974 | Margerum | |
| 3,808,006 A | 4/1974 | Smith | |
| 4,069,054 A | 1/1978 | Smith | |
| 4,069,055 A | 1/1978 | Crivello | |
| 4,216,288 A | 8/1980 | Crivello | |
| 4,250,053 A | 2/1981 | Smith | |
| 4,250,311 A | 2/1981 | Crivello | |
| 4,257,915 A | 3/1981 | Eaton | |
| 4,259,075 A | 3/1981 | Yamauchi et al. | |
| 4,356,296 A | 10/1982 | Griffith et al. | |
| 4,366,228 A | 12/1982 | Specht et al. | |
| 4,394,403 A | 7/1983 | Smith | |
| 4,455,147 A | 6/1984 | Lewis et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,642,126 A | 2/1987 | Zador et al. | |
| 4,650,913 A | 3/1987 | Feiring | |
| 4,652,274 A | 3/1987 | Boettcher et al. | |
| 4,665,217 A | 5/1987 | Reiners et al. | |
| 4,695,251 A | 9/1987 | Randklev | |
| 4,752,338 A | 6/1988 | Reiners et al. | |
| 4,755,620 A | 7/1988 | Iwamoto et al. | |
| 4,859,572 A | 8/1989 | Farid et al. | |
| 4,871,786 A | 10/1989 | Aasen et al. | |
| 4,872,936 A | 10/1989 | Engelbrecht | |
| 4,882,001 A | 11/1989 | Gonzalez et al. | |
| 4,908,227 A | 3/1990 | Dougherty et al. | |
| 4,959,297 A | 9/1990 | Palazzotto | |
| 4,966,934 A | 10/1990 | Huang et al. | |
| 4,971,892 A | 11/1990 | Ali et al. | |
| 4,983,644 A | 1/1991 | Mukai et al. | |
| 5,076,844 A | 12/1991 | Fock et al. | |
| 5,084,586 A | 1/1992 | Farooq | |
| 5,089,374 A | 2/1992 | Saeva | |
| 5,105,006 A * | 4/1992 | Parker .......................... | 562/30 |
| 5,124,417 A | 6/1992 | Farooq | |
| 5,130,347 A | 7/1992 | Mitra | |
| 5,154,762 A | 10/1992 | Mitra et al. | |
| 5,256,447 A | 10/1993 | Oxman et al. | |
| 5,304,585 A | 4/1994 | Bunker | |

(Continued)

FOREIGN PATENT DOCUMENTS

DE 2215474 10/1973

(Continued)

OTHER PUBLICATIONS

Connors, K. A.., "Chemical Kinetics, The Study of Reaction Rates in Solution", *VCH*, 1990, Chapter 2.

(Continued)

*Primary Examiner*—Susan W Berman
(74) *Attorney, Agent, or Firm*—Jean A. Lown

(57) ABSTRACT

Compositions are provided that include an electron donor and a sensitizing compound. More specifically, the electron donor is an arylsulfinate salt. Methods of polymerization are also provided that can be used to prepare polymeric material from a photopolymerizable composition that includes ethylenically unsaturated monomers and a photoinitiator system. The photoinitiator system includes an electron donor and a sensitizing compound.

14 Claims, No Drawings

U.S. PATENT DOCUMENTS

| | | | |
|---|---|---|---|
| 5,486,544 A * | 1/1996 | Kawashima et al. ........ 522/17 |
| 5,501,727 A | 3/1996 | Wang et al. |
| 5,530,038 A | 6/1996 | Yamamoto et al. |
| 5,545,676 A | 8/1996 | Palazzotto et al. |
| 5,607,663 A | 3/1997 | Rozzi et al. |
| 5,662,887 A | 9/1997 | Rozzi et al. |
| 5,739,177 A | 4/1998 | Ohno et al. |
| 5,866,630 A | 2/1999 | Mitra et al. |
| 5,876,208 A | 3/1999 | Mitra et al. |
| 5,888,491 A | 3/1999 | Mitra et al. |
| 5,998,495 A | 12/1999 | Oxman et al. |
| 6,017,660 A | 1/2000 | Palazzotto et al. |
| 6,030,606 A | 2/2000 | Holmes |
| 6,187,833 B1 | 2/2001 | Oxman et al. |
| 6,204,302 B1 | 3/2001 | Rawls et al. |
| 6,312,668 B2 | 11/2001 | Mitra et al. |
| 6,331,080 B1 | 12/2001 | Cole et al. |
| 6,387,981 B1 | 5/2002 | Zhang et al. |
| 6,444,725 B1 | 9/2002 | Trom et al. |
| 6,458,868 B1 | 10/2002 | Okada et al. |
| 6,528,555 B1 | 3/2003 | Nikutowski et al. |
| 6,566,413 B1 | 5/2003 | Weinmann et al. |
| 6,572,693 B1 | 6/2003 | Wu et al. |
| 6,624,236 B1 | 9/2003 | Bissinger et al. |
| 6,759,177 B2 | 7/2004 | Bissinger et al. |
| 6,777,460 B2 | 8/2004 | Palazzotto et al. |
| 7,026,367 B2 * | 4/2006 | Kalgutkar ............... 522/31 |
| 7,030,169 B2 * | 4/2006 | Kalgutkar et al. ......... 522/31 |
| 7,064,152 B2 | 6/2006 | Kalgutkar et al. |
| 7,250,452 B2 * | 7/2007 | Falsafi et al. ............ 523/115 |
| 7,329,692 B2 * | 2/2008 | Kalgutkar et al. ......... 522/25 |
| 7,465,758 B2 * | 12/2008 | Falsafi et al. ............ 522/17 |

FOREIGN PATENT DOCUMENTS

| | | |
|---|---|---|
| EP | 0 237 233 | 9/1987 |
| EP | 0 375 160 | 6/1990 |
| EP | 0 661 034 | 7/1995 |
| EP | 0 712 622 | 5/1996 |
| EP | 1 051 961 | 11/2000 |
| EP | 1 269 967 | 1/2003 |
| JP | 09-034110 | 2/1997 |
| JP | 2002-341519 | 11/2002 |
| WO | WO 01/07444 | 2/2001 |
| WO | WO 01/30306 | 5/2001 |
| WO | WO 01/30307 | 5/2001 |
| WO | WO 02/092021 | 11/2002 |

OTHER PUBLICATIONS

Rodrigues et al., "Cationic Photopolymerization Of Tetrahydrofuran: A Mechanistic Study On The Use Of A Sulfonium Salt-Phenothiazine Initiation System", *Journal of Polymer Science: Part A: Polymer Chemistry*, vol. 39, pp. 46-55, 2001.

Gomurashvili et al., "Phenothiazine Photosensitizers For Onium Salt Photoinitiated Cationic Polymerization", *Journal of Polymer Science: Part A: Polymer Chemistry*, vol. 39, pp. 1187-1197, 2001.

Crivello et al., "Dye-Sensitized Photoinitiated Cationic Polymerization. The System: Perylene-Triarylsulfonium Salts", *General Electric Corporate Research and Development*, Schenectady, NY, pp. 1059-1065.

"Pigments-Inorganic" and "Pigments-Organic", *Kirk-Othmer Encyclopedia of Chemical Technology*, Third ed., vol. 17, pp. 788-871, John Wiley & Sons, NY, 1982.

Pearson, "Photoconductive Polymers", *Pure and Appl. Chem.*, 49, pp. 463-477, 1977.

Beringer et al., "Diaryliodonium Salts. IX. The Synthesis of Substituted Diphenyliodonium Salts", *Am. Chem. Soc.*, 81, 342-351 (1959).

Dorman et al., "Carbon-13 Nuclear Magnetic Resonance Spectroscopy. Quantitative Correlations of the Carbon Chemical Shifts of Acyclic Alkenes", *J. Org. Chem.*, 36, 2757-2766 (1971).

Sims et al., "Studies on the Mechanism by Which Cyanine Dyes Measure Membrane Potential in Red Blood Cells and Phosphatidylcholine Vesicles", *Biochemistry*, vol. 13, No. 16, 3315-3330 (1974).

Safran et al., "Phase Diagrams for Microemulsions",*Phys.Rev.Lett.*, vol. 50, No. 24, pp. 1930-1933, (1983).

Buonocore et al., "A Report on A Resin Composition Capable Of Bonding To Human Dentin Surfaces", *J.Dent.Res.*, vol. 35, No. 6, pp. 846-851, (1956).

Leung et al., "Microemulsions: Formation, Structure, Properties, and Novel Applications", *Surfactants in Chemical/Process Engineering*, Marcel Dekker, Inc. NY, vol. 28, Chapter 9, pp. 315-367 (1988).

Ostrovsky et al., "Mechanism of Microemulsion Formation In Systems With Low Interfacial Tension: Occurrence, Properties, and Behavior of Microemulsions", *J.Colloid.Interface.Sci.*, vol. 102, No. 1, pp. 206-226 (1984).

Floyd J. Green, *The Sigma-Aldrich Handbook of Stains, Dyes and Indicators*, Aldrich Chemical Company, Inc., Milwaukee, WI (1990).

* cited by examiner

ARYLSULFINATE SALTS IN PHOTOINITIATOR SYSTEMS FOR POLYMERIZATION REACTIONS

CROSS REFERENCE TO RELATED APPLICATION

This application is a divisional of U.S. Ser. No. 11/380,028 filed 25 Apr. 2006, now U.S. Pat. No. 7,541,389, which is a divisional of U.S. Ser. No. 10/847,523 filed 17 May 2004 and issued as U.S. Pat. No. 7,064,152, which claims priority to U.S. Provisional Patent Application No. 60/506,396 filed on 26 Sep. 2003.

TECHNICAL FIELD

Arylsulfinate salts are provided that can be used as electron donors in initiator systems for free radical polymerization reactions.

BACKGROUND

Free radical polymerization reactions typically have an initiator system. In some applications, the initiator system is a photoinitiator system that can be based on various chemical approaches. For example, free radical polymerization reactions can be initiated using a three-component photoinitiator system that includes an electron acceptor, an electron donor, and a sensitizing compound. Alternatively, an electron donor in combination with a sensitizing compound can be used as a photoinitiator system.

In a three-component photoinitiator system that includes an electron donor, electron acceptor and a sensitizing compound, there is typically no direct reaction between the electron donor and the electron acceptor. Rather, the sensitizing compound usually absorbs actinic radiation resulting in the formation of an excited sensitizing compound. The electron donor can donate an electron to the excited sensitizing compound. That is, the sensitizing compound can reduced and the electron donor is oxidized. The reduced sensitizing compound can be a radical anion that can donate an electron to an electron acceptor to yield an initiating free radical for the polymerization reaction. The initiating free radical can be the reduced electron acceptor. In some instances of a three-component photoinitiator system, the oxidized electron donor can be a radical species that also functions as an initiating free radical.

Other photoinitiator systems have a sensitizing compound and an electron donor but no electron acceptor. The sensitizing compound can absorb actinic radiation to form an exited sensitizing compound. The electron donor can donate an electron to the excited sensitizing compound resulting in the oxidation of the electron donor. The oxidized electron donor can be a radical species that functions as an initiating free radical for polymerization reactions.

SUMMARY

Compositions are provided that include an electron donor and a sensitizing compound. More specifically, the electron donor is an arylsulfinate salt. Methods of polymerization are also provided that can be used to prepare polymeric material using a free radical polymerization reaction. The polymerization reaction is photoinitiated with a composition that includes an aryl sulfinate salt and a sensitizing compound.

One aspect of the invention provides a composition that includes an electron donor and a sensitizing compound capable of absorbing actinic radiation in the wavelength range of 250 to 1000 nanometers. The electron donor has an oxidation potential in N,N-dimethylformamide of 0.0 to +0.4 volts versus a silver/silver nitrate reference electrode and includes an arylsulfinate salt having an anion of Formula I

and having a cation containing at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The composition can further include ethylenically unsaturated monomers.

A second aspect of the invention provides a photopolymerization method that includes irradiating a photopolymerizable composition with actinic radiation until the photopolymerizable composition gels or hardens. The photopolymerizable composition includes an ethylenically unsaturated monomer, a sensitizing compound, and an electron donor. The sensitizing compound is capable of absorbing a wavelength of actinic radiation in the range of 250 to 1000 nanometers. The electron donor has an oxidation potential in N,N-dimethylformamide of 0.0 to +0.4 volts versus a silver/silver nitrate reference electrode and includes an arylsulfinate salt. The arylsulfinate salt has an anion of Formula I

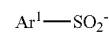

and a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

Another aspect of the invention provides arylsulfinate salts. In one embodiment of the compounds, the arylsulfinate salt has an anion of Formula I

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The cation of the arylsulfinate salt is of Formula II

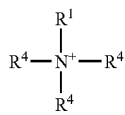

where $R^1$ is an alkyl or aryl and each $R^4$ is independently hydrogen, alkyl or aryl. The $R^1$ and $R^4$ groups can be unsubstituted or substituted. An alkyl group can be substituted with a hydroxy. An aryl can be substituted with a hydroxy, alkyl, or combinations thereof.

In another embodiment of the compounds, the arylsulfinate salt has an anion of Formula I

$$Ar^1\text{—}SO_2^- \quad\quad\quad I$$

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The cation of the arylsulfinate salt is a ring structure that includes a 4 to 12 member heterocyclic group with a positively charged nitrogen atom and at least one other heteroatom selected from nitrogen, oxygen, sulfur, or combinations thereof. The heterocyclic group can be saturated or unsaturated. The cationic ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

In yet another embodiment of the compounds, the arylsulfinate salt has an anion of Formula I

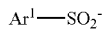

$$Ar^1\text{—}SO_2^- \quad\quad\quad I$$

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The cation of the arylsulfinate salt is of Formula III

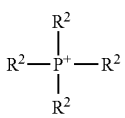

where each $R^2$ is independently an alkyl or aryl that is unsubstituted or substituted. An alkyl can be substituted with a hydroxy. An aryl can be substituted with a hydroxy, alkyl, or combinations thereof.

The above summary is not intended to describe each disclosed embodiment or every implementation of the present invention. The detailed description section that follows more particularly exemplifies these embodiments.

DETAILED DESCRIPTION

Compositions are provided that include an electron donor and a sensitizing compound. More specifically, the electron donor is an arylsulfinate salt. Methods of polymerization are also provided that can be used to prepare polymeric material from a photopolymerizable composition that includes ethylenically unsaturated monomers and a photoinitiator system. The photoinitiator system includes an electron donor and a sensitizing compound.

DEFINITIONS

As used herein, the terms "a", "an", and "the" are used interchangeably with "at least one" to mean one or more of the elements being described.

As used herein, the term "actinic radiation" refers to electromagnetic radiation capable of producing photochemical activity.

As used herein, the term "acyl" refers to a monovalent group of formula —(CO)$R^a$ where $R^a$ is an alkyl or aryl group.

As used herein, the term "alkenyl" refers to a monovalent radical of an alkene (i.e., an alkene is an aliphatic compound having at least one carbon-carbon double bond).

As used herein, the term "alkoxy" refers to a group of formula —OR where R is an alkyl group. Examples include methoxy, ethoxy, propoxy, butoxy, and the like.

As used herein, the term "alkoxycarbonyl" refers to a monovalent group of formula —(CO)OR where R is an alkyl group. An example is ethoxycarbonyl.

As used herein, the term "alkoxysulfonyl" refers to a monovalent group having the formula —SO$_3$R where R is an alkyl group.

As used herein, the term "alkyl" refers to a monovalent radical of an alkane. The alkyl can be linear, branched, cyclic, or combinations thereof and typically contains 1 to 30 carbon atoms. In some embodiments, the alkyl group contains 1 to 20, 1 to 14, 1 to 10, 4 to 10, 4 to 8, 1 to 6, or 1 to 4 carbon atoms. Examples of alkyl groups include, but are not limited to methyl, ethyl, n-propyl, isopropyl, n-butyl, tert-butyl, isobutyl, n-pentyl, n-hexyl, cyclohexyl, n-octyl, n-heptyl, and ethylhexyl.

As used herein, the term "alkylsulfonyl" refers to a monovalent group of formula —SO$_2$R where R is an alkyl group.

As used herein, the term "alkynyl" refers to a monovalent radical of an alkyne (i.e., an alkyne is an aliphatic compound having at least one carbon-carbon triple bond).

As used herein, the term "amino" refers to a monovalent group of formula —NR$^b_2$ where each R$^b$ is independently a hydrogen, alkyl, or aryl group. In a primary amino group, each R$^b$ group is hydrogen. In a secondary amino group, one of the R$^b$ groups is hydrogen and the other R$^b$ group is either an alkyl or aryl. In a tertiary amino group, both of the R$^b$ groups are an alkyl or aryl.

As used herein, the term "aminocarbonyl" refers to a monovalent group of formula —(CO)NR$^b_2$ where each R$^b$ is independently a hydrogen, alkyl, or aryl.

As used herein, the term "aromatic" refers to both carbocyclic aromatic compounds or groups and heteroaromatic compounds or groups. A carbocyclic aromatic compound is a compound that contains only carbon atoms in an aromatic ring structure. A heteroaromatic compound is a compound that contains at least one heteroatom selected from S, O, N, or combinations thereof in an aromatic ring structure.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "aryloxy" refers to a monovalent group of formula —OAr where Ar is an aryl group.

As used herein, the term "aryloxycarbonyl" refers to a monovalent group of formula —(CO)OAr where Ar is an aryl group.

As used herein, the term "aryloxysulfonyl" refers to a monovalent group having the formula —$SO_3$Ar where Ar is an aryl group.

As used herein, the term "azo" refers to a divalent group of formula —N=N—.

As used herein, the term "carbonyl" refers to a divalent group of formula —(CO)— where the carbon atom is connected to the oxygen atom by a double bond.

As used herein, the term "carboxy" refers to a monovalent group of formula —(CO)OH.

As used herein, the term "conjugated" refers to unsaturated compounds having at least two carbon-carbon double or triple bonds with alternating carbon-carbon single bonds and carbon-carbon double or triple bonds.

As used herein, the term "cyano" refers to a group of formula —CN.

As used herein, the term "dialkylphosphonato" refers to a group of formula —(PO)(OR)$_2$ where R is an alkyl. The formula "(PO)" indicates that the phosphorus atom is bonded to an oxygen atom with a double bond.

As used herein, the term "diarylphosphonato" refers to a group of formula —(PO)(OAr)$_2$ where Ar is a aryl.

As used herein, the term "electron donating" refers to a substituent that can donate electrons. Suitable examples include, but are not limited to, a primary amino, secondary amino, tertiary amino, hydroxy, alkoxy, aryloxy, alkyl, or combinations thereof.

As used herein, the term "electron withdrawing" refers to a substituent that can withdraw electrons. Suitable examples include, but are not limited to, a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

As used herein, the term "fluoroalkyl" refers to an alkyl group that has at least one hydrogen atom replaced with a fluorine atom.

As used herein, the term "formyl" refers to a monovalent group of formula —(CO)H where the carbon is attached to the oxygen atom with a double bond.

As used herein, the term "halo" refers to a halogen group (i.e., F, Cl, Br, or I). In some embodiments, the halo group is F or Cl.

As used herein, the term "halocarbonyl" refers to a monovalent group of formula —(CO) X where X is a halogen group (i.e., F, Cl, Br, or I).

As used herein, the term "heteroaryl" refers to a monovalent radical having a five to seven member aromatic ring that includes one or more heteroatoms independently selected from S, O, N, or combinations thereof in the ring. Such a heteroaryl ring can be connected to or fused to up to five ring structures that are aromatic, aliphatic, or combinations thereof. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, and indazolyl, and the like. A heteroaryl is a subset of a heterocyclic group.

As used herein, the term "heterocyclic" refers to a monovalent radical having a ring structure that is saturated or unsaturated and that includes one or more heteroatoms independently selected from S, O, N, or combinations thereof in the ring. The heterocyclic group can be a single ring, bicyclic, or can be fused to another cyclic or bicyclic group. The fused cyclic or bicyclic group can be saturated or unsaturated and can be carbocyclic or contain heteroatoms.

As used herein, the term "hydroxy" refers to a group of formula —OH.

As used herein, the term "mercapto" refers to a group of formula —SH.

As used herein, the term "perfluoroalkyl" refers to an alkyl group that has all the hydrogen atoms replaced with fluorine atoms. A perfluoroalkyl is a subset of a fluoroalkyl.

As used herein, the term "perfluoroalkylsulfonyl" refers to a monovalent group of formula —$SO_2R_f$ where $R_f$ is a perfluoroalkyl.

As used herein, the term "polymerization" refers to forming a higher weight material from monomer or oligomers. The polymerization reaction also can involve a cross-linking reaction.

As used herein when referring to a composition containing an initiator system and polymerizable material, the term "shelf-stable" means that the composition can be stored for at least one day without any visible gel formation at room temperature (i.e., 20° C. to 25° C.).

As used herein when referring to a compound, the term "oxidative stability" refers to the length of time needed to oxidize 50 weight percent of the compound ($t_{1/2}$) at room temperature (i.e., 20° C. to 25° C.) which can be calculated using pseudo-first order kinetics as described in K. A. Connors, *Chemical Kinetics: The Study of Reaction Rates in Solution*, Chapter 2, VCH, New York, 1990.

As used herein, the term "sulfo" refers to a group having the formula —$SO_3H$.

Compositions

A variety of materials are known for use as an electron donor in initiator systems for polymerization reactions. However, some of these materials have limited solubility in ethylenically unsaturated monomers. Further, some of these materials have limited oxidative stability, shelf-stability, or combinations thereof.

One aspect of the invention provides a composition that includes an electron donor and a sensitizing compound. More specifically, the electron donor includes an arylsulfinate salt. The compositions can be used as photoinitiator systems for free radical polymerization reactions.

The electron donor has an oxidation potential in N,N-dimethylformamide of 0.0 to +0.4 volts versus a silver/silver nitrate reference electrode and is an arylsulfinate salt having an anion of Formula I $$Ar^1-SO_2^- \qquad \qquad I$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

The electron donor is selected to have an oxidation potential in a stated range. The oxidation potential can be determined using cyclic voltammetry. As described herein, the oxidation potential is measured by dissolving the compound of interest in a non-aqueous solvent (i.e., N,N-dimethylformamide) containing a supporting electrolyte (i.e., 0.1 moles/liter tetrabutylammonium hexafluorophosphate). The resulting solution is purged with an inert gas such as argon. A three-electrode configuration is used that includes a working electrode (i.e., a glassy carbon electrode), a reference electrode (i.e., a silver wire in a 0.01 moles/liter of silver nitrate dissolved in acetonitrile), and a counter electrode (i.e., a platinum wire). The oxidation or reduction potential is the voltage corresponding to the maximum current for the oxidation reaction.

One component of the composition is the electron donor. The electron donor is an arylsulfinate salt having an anion of Formula I

$$Ar^1\!-\!SO_2^-  \qquad \text{I}$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The arylsulfinate salt is typically soluble in monomers capable of undergoing free radical polymerization reactions and in a variety of non-polar and polar solvents. As used herein, the term "soluble" refers to a compound that can be dissolved in an amount at least equal to 0.05 moles/liter, at least 0.07 moles/liter, at least 0.08 moles/liter, at least 0.09 moles/liter, or at least equal to 0.1 moles/liter in a given material such as a solvent or monomer.

In some arylsulfinate salts, the $Ar^1$ group is a substituted phenyl or an unsubstituted or substituted $C_{7-30}$ aryl group having a carbocyclic aromatic ring. The aryl group can have a single carbocyclic aromatic ring or can have additional carbocyclic rings that are fused or connected to the carbocyclic aromatic ring. Any fused or connected rings can be saturated or unsaturated. The aryl often contains up to 5 rings, up to 4 rings, up to 3 rings, up to 2 rings, or one ring. The aryl group usually has up to 30 carbon atoms, up to 24 carbon atoms, up to 18 carbon atoms, up to 12 carbon atoms, or 6 carbon atoms. Examples of aryl groups having a single ring or multiple fused rings include, but are not limited to, phenyl, anthryl, naphthyl, acenaphthyl, phenanthryl, phenanthrenyl, perylenyl, and anthracenyl. A single bond, methylene group (i.e., $-C(R^b)_2-$ where each $R^b$ is independently hydrogen, aryl, or alkyl), carbonyl group (i.e., $-(CO)-$), or combinations thereof can connect multiple rings. Examples of aryl groups having multiple connected rings include, but are not limited to, anthraquinonyl, anthronyl, biphenyl, terphenyl, 9,10-dihydroanthracenyl, and fluorenyl.

In other arylsulfinate salts, the $Ar^1$ group in Formula I can be an unsubstituted or substituted heteroaryl that has a five to seven member aromatic ring that contains one or more heteroatoms independently selected from S, O, N, or combinations thereof in the ring. The heteroaryl can have a single ring or can have multiple rings connected or fused together. Any additional connected or fused rings can be carbocyclic or contain a heteroatom and can be saturated or unsaturated. The heteroaryl group often has up to 5 rings, up to 4 rings, up to 3 rings, up to 2 rings, or one ring. The heteroaryl typically contains up to 30 carbon atoms. In some embodiments, the heteroaryl contains up to 20 carbon atoms, up to 10 carbon atoms, or up to 5 carbon atoms. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, azaphenanthrenyl, and indazolyl.

The $Ar^1$ group in Formula I can be substituted with an electron withdrawing group or an electron withdrawing group in combination with an electron donating group provided that the arylsulfinate salt has an oxidation potential in N,N-dimethylformamide of 0.0 to +0.4 volts versus a silver/silver nitrate reference electrode. Electron donating groups can be selected, for example, from a primary amino, secondary amino, tertiary amino, hydroxy, alkoxy, aryloxy, alkyl, or combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

In some embodiments, the $Ar^1$ group includes an electron withdrawing group that is conjugated to the sulfinate group. For example, the $Ar^1$ group can be a phenyl substituted with an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

Specific examples of the arylsulfinate anion of Formula I include, but are not limited to, 4-chlorobenzenesulfinate, 4-cyanobenzenesulfinate, 4-ethoxycarbonylbenzenesulfinate, 4-trifluoromethylbenzenesulfinate, 3-trifluoromethylbenzenesulfinate, 1-naphthalenesulfinate, 2-naphthalenesulfinate, and 1-anthraquinonesulfinate.

The arylsulfinate salts have a cation with at least one carbon atom and either a positively charged nitrogen atom or a positively charged phosphorus atom. In one embodiment, the cation of the arylsulfinate is of Formula II

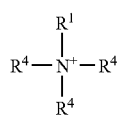

where $R^1$ is an alkyl or aryl and each $R^4$ is independently a hydrogen, alkyl, or aryl. The $R^1$ and $R^4$ groups can be unsubstituted or substituted. An alkyl group can be substituted with a hydroxy. An aryl can be substituted with an alkyl, hydroxy, or combinations thereof.

In some examples of Formula II, $R^1$ and each $R^4$ group are independently a $C_{2-30}$ alkyl that is unsubstituted or substituted with a hydroxy. For example, $R^1$ and each $R^4$ independently can be an alkyl group having up to 20, up to 10, up to 8, up to 6, or up to 4 carbon atoms. The alkyl group often has at least 2, at least 3, at least 4, at least 6, or at least 8 carbon atoms. The alkyl group can have 4 to 30, 8 to 30, 3 to 10, 4 to 10, 4 to 8, or 4 to 6 carbon atoms in some compounds. In a specific example, the cation of the arylsulfinate salt is a tetrabutylammonium ion.

In other examples of Formula II, $R^1$ and two $R^4$ groups are each independently a $C_{2-30}$ alkyl that can be unsubstituted or substituted with a hydroxy. The remaining $R^4$ group is hydrogen. In still other examples, $R^1$ and one $R^4$ group are each independently a $C_{4-30}$ alkyl that is unsubstituted or substituted with a hydroxy; and the two remaining $R^4$ groups are hydrogen. In yet other examples, $R^1$ is a $C_{8-30}$ alkyl that is unsubstituted or substituted with a hydroxy; and the $R^4$ groups are hydrogen.

The $R^1$ group and each of the $R^4$ groups in Formula II independently can be an aryl group that is unsubstituted or substituted with an alkyl, hydroxy, or combinations thereof. An exemplary cation is tetraphenylammonium ion. In another example, $R^1$ and one $R^4$ are independently an aryl group that is unsubstituted or substituted with an alkyl, hydroxy, or combinations thereof, and the two remaining $R^4$ groups are hydrogen. An exemplary cation is diphenylammonium ion.

In other embodiments, the cation of the arylsulfinate salt is a ring structure that includes a 4 to 12 member heterocyclic group with a positively charged nitrogen atom. The heterocyclic group can be saturated or unsaturated and can contain up to three heteroatoms selected from nitrogen, oxygen, sulfur, or combinations thereof (i.e., there is one positively charged nitrogen atom and up to two other heteroatoms selected from nitrogen, oxygen, sulfur, or combinations thereof). The ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

The heterocyclic group in the cationic ring structure can be a single ring, bicyclic, or can be fused to another cyclic or bicyclic group. The fused cyclic or bicyclic group can be saturated or unsaturated and can have 0 to 3 heteroatoms. The ring structure can include up to 30 carbon atoms, up to 24 carbon atoms, up to 18 carbon atoms, up to 12 carbon atoms, up to 6 carbon atoms, or up to 4 carbon atoms and up to 6 heteroatoms, up to 4 heteroatoms, up to 2 heteroatoms, or 1 heteroatom. In some embodiments, the ring structure is a 4 to 12 member heterocyclic group that is a fused to an aromatic ring having 0 to 3 heteroatoms. The heterocyclic group is bicyclic in some examples.

Suitable examples of five member heterocyclic groups that contain a positively charged nitrogen atom include, but are not limited to, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, and oxathiazolium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is an imidazolium ion or oxazolium ion that is unsubstituted or substituted.

The five member heterocyclic groups can be fused to another cyclic group. In some exemplary ring structures, a five membered heterocyclic group is fused to an aromatic group. Exemplary ring structures include, but are not limited to, an indole ion, indazolium ion, benzopyrrolidinium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, carbozolium ion, and purinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is a benzoxazolium ion or a benzothiazolium ion that is unsubstituted or substituted.

Suitable examples of six member heterocyclic groups that contain a positively charged nitrogen atom include, but are not limited to, a pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof. In some applications, the cation is a pyridinium ion or a morpholinium ion that is unsubstituted or substituted.

The six member heterocyclic groups can be fused to another cyclic group. In some exemplary ring structures, a six membered heterocyclic group is fused to an aromatic group. Exemplary ring structures include, but are not limited to, isoquinolinium ion, quinolinium ion, cinnolinium ion, quinazolinium ion, benzopyrazinium ion, benzopiperazinium ion, benzotriazinium ion, benzoxazinium ion, benzopiperidinium ion, benzoxathiazinium ion, benzoxadizinium ion, benzomorpholinium ion, naphtyridinium ion, and acridinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof.

Suitable examples of seven member heterocyclic groups that contain a positively charged nitrogen atom include, for example, an azepinium ion and diazepinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

Examples of heterocyclic groups that are bicyclic include, but are not limited to, N-alkylated or N-protonated 1,4-diazabicyclo [2.2.2] octane and N-alkylated or N-protonated 1-azabicyclic [2.2.2] octane that is unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

In other embodiments, the cation of the arylsulfinate salt contains a positively charged phosphorus atom of Formula III

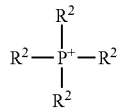

III where each $R^2$ is independently an alkyl or aryl that is unsubstituted or substituted. An alkyl group can be substituted with a hydroxy. An aryl can be substituted with an alkyl, hydroxy, or combinations thereof.

In some examples of Formula III, all of the $R^2$ groups are an aryl group. For example, the cation can be a tetraphenylphosphonium ion. In other examples, one, two, or three of the $R^2$ groups are an aryl with the remaining $R^2$ group or groups being a $C_{2-30}$ alkyl.

Some of the arylsulfinate salts can have an anion of Formula IV

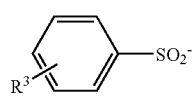

IV and a cation that includes a positively charged nitrogen atom. In Formula IV, $R^3$ can be in an ortho, para, or meta position of the benzene ring and is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or aminocarbonyl. In some compounds, $R^3$ is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, or alkylsulfonyl. In other compounds, $R^3$ is a halo, cyano, or alkoxycarbonyl group.

Specific examples Formula IV where $R^3$ is located in the para position of the phenyl ring include 4-cyanobenzenesulfinate, 4-chlorobenzenesulfinate, 4-ethoxycarbonylbenzenesulfinate, and 4-trifluoromethylbenzenesulfinate. A specific example of $R^3$ located in the meta position of the phenyl ring includes 3-trifluoromethylbenzenesulfinate.

For some applications, the arylsulfinate salt includes an anion of Formula IV and a cation that is a tetraalkyammonium ion. The alkyl groups of the tetraalkylammonium ion can be the same or different and typically contain 2 to 30 carbon atoms. For example, the alkyl groups can contain 4 to 30 carbon atoms, 8 to 30 carbon atoms, 3 to 10 carbon atoms, 4 to 10 carbon atoms, 4 to 8 carbon atoms, or 4 to 6 carbon atoms. Specific arylsulfinate salts include, but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, and tetrabutylammonium 3-trifluoromethylbenzenesulfinate.

Other specific examples of electron donors include, but are not limited to, tetrabutylammonium 1-naphthalenesulfinate, tetrabutylammonium 2-naphthalenesulfinate, and tetrabutylammonium 1-anthraquinonesulfinate, 1-ethyl-3-methylimidazolium 4-cyanobenzenesulfinate, N,N-dimethylmorpholinium 4-cyanobenzenesulfinate, 3-ethyl-2-methylbenxoxazolium 4-cyanobenzenesulfinate, 1-methyl-4-aza-1-azoniabicyclo[2.2.2]octane 4-cyanobenzenesulfinate, and N-hexadecylpyridinium 4-cyanobenzenesulfinate.

Another component of the compositions is a sensitizing compound that is capable of absorbing actinic radiation in the range of 250 to 1000 nanometers. In some embodiments, the sensitizing compound can absorb actinic radiation in the range of 300 to 1000 nanometers, in the range of 350 to 1000 nanometers, in the range of 250 to 850 nanometers, in the range of 250 to 800 nanometers, in the range of 400 to 800 nanometers, in the range of 425 to 800 nanometers, or in the range of 450 to 800 nanometers.

Suitable sensitizing compounds that are dyes include, but are not limited to, ketones (e.g., monoketones and diketones), coumarin dyes (e.g., ketocoumarins such as Coumarin 153), xanthene dyes (e.g., Rose Bengal and Rhodamine 6G), acridine dyes, thiazole dyes, thiazine dyes (e.g., Methylene Blue and Methylene Violet), oxazine dyes (e.g., Basic Blue 3 and Nile Blue Chloride), azine dyes (e.g., Methyl Orange), aminoketone dyes, porphyrins (e.g., porphyrazine), aromatic polycyclic hydrocarbons, p-substituted aminostyryl ketone compounds, aminotriaryl methanes, cyanine dyes (e.g., the cyanine dye described in *Biochemistry*, 12, 3315 (1974)), squarylium dyes, pyridinium dyes, benzopyrilium dyes, and triarylmethane (e.g., Malachite Green). In some applications, the sensitizing compounds include xanthenes, monoketones, diketones, or combinations thereof. Other suitable sensitizing dyes are described in F. J. Green, The *Sigma-Aldrich Handbook of Stains, Dyes, and Indicators*, Aldrich Chemical Company, Inc., Milwaukee, Wis. (1990).

In some embodiments, the sensitizing compound is a xanthene dye such as fluoresceins, rhodamines, eosins, and pyronins.

Exemplary monoketones include 2,2-dihydroxybenzophenone, 4,4-dihydroxybenzophenone, 2,4-dihydroxybenzophenone, di-2-pyridyl ketone, di-2-furanyl ketone, di-2-mercaptophenyl ketone, benzoin, fluorenone, chalcone, Michler's ketone, 2-fluoro-9-fluorenone, 2-chloromercaptoxanthone, acetophenone, benzophenone, 1- or 2-acetonaphthone, 9-acetylanthracene, 2-, 3-, or 9-acetylphenanthrene, 4-acetylbiphenyl, propiophenone, n-butyrophenone, valerophenone, 2-, 3-, or 4-acetylpyridine, 3-acetylcoumarin, and the like.

Exemplary diketones include aralkyldiketones such as anthraquinone, phenanthrenequinone, o-, m-, and p-diacetylbenzene, 1,3-, 1,4-, 1,5-, 1,6-, 1,7-, and 1-8 diacetylnaphthalene, 1,5-, 1,8-, and 9,10-diacetylanthracene, and the like. Exemplary alpha-diketones include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-, 3,3'-, and 4,4'-dihydroxybenzil, furil, di-3,3'-indolylethanedione, 2,3-bornanedione (camphorquinone), biacetyl, 1,2-cyclohexanedione, 1,2-naphthaquinone, acenaphthaquinone, and the like.

The dye can have a molar extinction coefficient up to about 150,000 1-mole$^{-1}$cm$^{-1}$. In some applications, the dye has a molar extinction coefficient that is up to 85,000 1-mole$^{-1}$cm$^{-1}$, up to 70,000, up to 50,000, up to 30,000, up to 10,000, or up to 5,000 1-mole$^{-1}$cm$^{-1}$.

For applications requiring deep cure (e.g., cure of highly filled composites such as dental composites or cure of a thick sample), a sensitizing compound is typically selected that has an extinction coefficient less than 1000 1-mole$^{-1}$cm$^{-1}$. In some examples, the extinction coefficient at the wavelengths of actinic radiation used for photopolymerization is less than 500 or less than 100 1-mole$^{-1}$cm$^{-1}$. The alpha-diketones, for example, are sensitizing compounds that can be used for such applications.

The sensitizing compound also can be a pigment as described in U.S. Pat. Nos. 4,959,297 and 4,257,915, the disclosures of which are incorporate herein by reference in their entirety. Suitable inorganic pigments include, but are not limited to, titanium dioxide, strontium titanate, barium titanate, zinc oxide, zinc sulfide, zinc selenide, cadmium sulfide, cadmium selenide, cadmium telluride, or combinations thereof. Suitable organic pigments include, but are not limited to, phthalocyanine blue (pigment blue 15), copper polychlorophthalocyanine green (pigment green 7), copper polybromochlorophthalocyanine (pigment green 36), perylene scarlet (vat red 29), perylene vermillion (pigment red 23), perylene maroon, perylene Bordeaux, perylene dianhydride (perylene red), and those described in "Pigments-Inorganic" and "Pigments-Organic" in *Kirk-Othmer Encyclopedia of Chemical Technology*, Third ed., Volume 17, pp. 788-817, John Wiley and Sons, New York, 1982. The organic pigments also can be semiconducting polymers as described by Y. M. Paushkin et al., *Organic Polymeric Semiconductors*, John Wiley & Sons, New York, 1974 and by J. M. Pearson, *Pure and Appl. Chem.*, 49, 463-477 (1977).

The composition can further include monomers that can be polymerized using a free-radical polymerization reaction. The monomers typically contain at least one ethylenically-unsaturated double bond. The monomers, for example, can be monoacrylates, diacrylates, polyacrylates, monomethacrylates, dimethacrylates, polymethacrylates, or combinations thereof. The monomers can be unsubstituted or substituted with a hydroxy. Exemplary monomers include methyl acrylate, methyl methacrylate, ethyl acrylate, ethyl methacrylate, isopropyl acrylate, isopropyl methacrylate, n-hexyl acrylate, stearyl acrylate, allyl acrylate, glycerol acrylate, glycerol diacrylate, glycerol triacrylate, ethyleneglycol diacrylate, diethyleneglycol diacrylate, triethyleneglycol diacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane, and tris-hydroxyethyl-isocyanurate trimethylacrylate. The monomers also can be bis-acrylates and bis-methacrylates of polyethylene glycol having an average molecular weight ($M_n$) of 200 to 500; copolymerizable mixtures of acrylated monomers such as those described in U.S. Pat. No. 4,652,274, incorporated herein by reference in its entirety; acrylated monomers such as those described in U.S. Pat. No. 4,642,126, incorporated herein by reference in its entirety; unsaturated amides such as methylene bis-arylamide, methylene bis-methacrylamide, 1,6-hexamethylene bis-acrylamide, diethylene triamine tris-acrylamide, and beta-methacrylaminoethyl methacrylate; and vinyl monomers such as styrene, diallyl phthalate, divinyl succinate, divinyl adipate, and divinylphthalate. Mixtures of two or more monomers can be used, if desired.

The electron donor and the sensitizing compound can be present in an amount effective to enable free radical polymerization of the ethylenically-unsaturated monomers. In some applications, the electron donor can be present in an amount up to 4 weight percent, up to 3 weight percent, up to 2 weight percent, up to 1 weight percent, or up to 0.5 weight percent based on the weight of the monomers. For example, the electron donor can be present in an amount of 0.1 to 4 weight percent, 0.1 to 3 weight percent, 0.1 to 2 weight percent, or 0.5 to 1 weight percent based on the weight of the monomers.

The sensitizing compound is often used in an amount up to 4 weight percent based on the weight of the monomers. In some applications, the sensitizing compound is present in an amount up to 3 weight percent, up to 2 weight percent, up to 1 weight percent, up to 0.5 weight percent based on the weight of the monomers. For example, the sensitizing compound can be present in an amount of 5 ppm to 4 weight percent, 10 ppm to 2 weight percent, 15 ppm to 1 weight percent, or 20 ppm to 0.5 weight percent based on the weight of the monomers.

The compositions can contain a wide variety of additives depending on the desired use of the polymerized material. Suitable additives include solvents, diluents, resins, binders, plasticizers, inorganic and organic reinforcing or extending fillers, thixotropic agents, UV absorbers, medicaments, and the like.

The compositions are typically free of an electron acceptor such as metal ions in an oxidized state, persulfates, peroxides, iodonium salts, hexaarylbisimidazoles, or combinations thereof.

In some embodiments, the components of the compositions can be selected to provide a useful combination of cure speed, cure depth, and shelf life. Some compositions can cure well even when loaded with large amounts of fillers. The compositions can be used to form foams, shaped articles, adhesives, filled or reinforced composites, abrasives, caulking and sealing formulations, casting and molding formulations, potting and encapsulating formulations, impregnating and coating formulations, and the like.

Suitable applications for the compositions include, but are not limited to, graphic arts imaging (e.g., for color proofing systems, curable inks, and silverless imaging), printing plates (e.g., for projection plates and laser plates), photoresists, solder masks for printed circuit boards, coated abrasives, magnetic media, photocurable adhesives (e.g., for orthodontics and general bonding applications), photocurable composites (e.g., for autobody repair and dental restoratives), protective coatings, and abrasion resistant coatings. The compositions are also suitable for use in a multi-photon process, where high intensity/short pulse lasers are used in combination with suitable dyes and co-reactants to produce polymerizable compositions that are useful for imaging, microreplication and stereolithographic applications. The compositions can be used in other applications that are known to those skilled in the art.

Polymerization Methods

The invention also provides methods for photopolymerizing ethylenically unsaturated monomers using free radical polymerization reactions. The photopolymerization method includes irradiating a photopolymerizable composition with actinic radiation until the photopolymerizable composition gels or hardens. The photopolymerizable composition includes a photoinitiator system and monomers capable of undergoing free radical polymerization reactions (i.e., ethylenically unsaturated monomers). The photoinitiator system includes an electron donor and a sensitizing compound. In some embodiments of the photopolymerizable composition, the components can be mixed together and stored for at least one day prior to use.

The electron donor in the photoinitiator system includes an arylsulfinate salt having an anion of Formula I

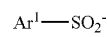

$$Ar^1 \!-\! SO_2^-\qquad\qquad I$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The electron donor has an oxidation potential in N,N-dimethylformamide of 0.0 to +0.4 volts versus a silver/silver nitrate reference electrode.

In some embodiments, the oxidization potential in N,N-dimethylformamide is +0.08 to +0.4 volts, +0.08 to +0.3 volts, or +0.08 to +0.2 volts versus a silver/silver nitrate reference electrode.

The photopolymerizable compositions can include a wide variety of different types of sensitizing compounds such as dyes, organic pigments, inorganic pigments, or combinations thereof. In some embodiments, the sensitizing compound can change colors indicating that the polymeric material has been cured. The color changes can be attributed to chemical alterations to the sensitizing compound.

The photoinitiator system can be activated by exposing the sensitizing compound to actinic radiation having a wavelength in the range of 250 to 1000 nanometers. In some applications, the actinic radiation has a wavelength in the range of 300 to 1000 nanometers, in the range of 350 to 1000 nanometers, in the range of 250 to 850 nanometers, in the range of 250 to 800 nanometers, in the range of 400 to 800 nanometers, in the range of 425 to 800 nanometers, or in the range of 450 to 800 nanometers. An excited sensitizing compound is formed upon exposure to the actinic radiation. The electron donor can donate an electron to the excited sensitizing compound. The sensitizing compound is reduced and the electron donor is oxidized. The oxidized electron donor is a radical species that can function as an initiating free radical for the polymerization reaction.

Monomers suitable for photopolymerization methods typically include an ethylenically unsaturated monomer such as a monoacrylate, monomethacrylate, diacrylate, dimethacrylate, polyacrylate, polymethacrylate, or combinations thereof.

In some embodiments, visible light can be used to excite the sensitizing compound and activate the photopolymerizable composition. This can be advantageous because relatively inexpensive light sources can be used. Light sources emitting in the visible region of the electromagnetic spectrum tend to be less expensive than those emitting, for example, in the ultraviolet region. Other light sources that include ultraviolet radiation or a combination of ultraviolet and visible radiation also can be used. Typical light sources include, but are not limited to, mercury vapor discharge lamps, carbon arcs, tungsten lamps, xenon lamps, sunlight, lasers, light emitting diodes, and the like.

Arylsulfinate Compounds

Another aspect of the invention provides arylsulfinate salts. In one embodiment, the arylsulfinate salts have an anion of Formula I

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The cation of the arylsulfinate salt is of Formula II

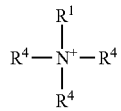

where $R^1$ is independently an alkyl or aryl and each $R^4$ is independently hydrogen, alkyl, or aryl. The $R^1$ and $R^4$ groups can be unsubstituted or substituted. An alkyl group can be substituted with a hydroxy. An aryl group can be substituted with a hydroxy, alkyl, or combinations thereof.

In other examples of Formula II, $R^1$ and two $R^4$ groups are each independently a $C_{2-30}$ alkyl that can be unsubstituted or substituted with a hydroxy. The remaining $R^4$ group is hydrogen. In still other examples, $R^1$ and one $R^4$ group are each independently a $C_{4-30}$ alkyl that is unsubstituted or substituted with a hydroxy; and the two remaining $R^4$ groups are hydrogen. In yet other examples, $R^1$ is a $C_{8-30}$ alkyl that is unsubstituted or substituted with a hydroxy; and the $R^4$ groups are hydrogen.

In other examples of Formula II, $R^1$ and at least some of the $R^4$ groups include an aryl group such as a phenyl group. An exemplary cation is tetraphenylammonium ion.

Some specific arylsulfinate salts that include an anion of Formula I and a cation of Formula II include, but are not limited to, tetrabutylammonium 1-naphthalenesulfinate, tetrabutylammonium 2-naphthalenesulfinate, and tetrabutylammonium 1-anthraquinonesulfinate.

The arylsulfinate salt can have an anion of Formula IV

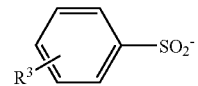

where $R^3$ can be on an ortho, para, or meta position of the benzene ring. The $R^3$ group is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, or combinations thereof. The choice and location of the electron withdrawing group on the ring can affect the oxidation potential of the arylsulfinate salt. Specific examples of cations of Formula IV include 4-cyanobenzenesulfinate, 4-chlorobenzenesulfinate, 4-ethoxycarbonylbenzenesulfinate, 4-trifluoromethylbenzenesulfinate, and 3-trifluoromethylbenzenesulfinate.

For some applications, the arylsulfinate salt includes an anion of Formula IV and a cation that is a tetraalkylammonium ion. The alkyl groups can be the same or different and typically contains 1 to 10 carbon atoms. For example, the alkyl groups can contain 3 to 10 carbon atoms, 4 to 10 carbon atoms, 4 to 8 carbon atoms, or 4 to 6 carbon atoms. Specific arylsulfinate salts include but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, and tetrabutylammonium 3-trifluoromethylbenzenesulfinate.

In other embodiments of an arylsulfinate salt, the anion is of Formula I

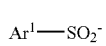

as described above and the cation is a ring structure that includes a 4 to 12 member heterocyclic group having a positively charged nitrogen atom. In addition to the positively charged nitrogen heteroatom, the heterocyclic ring contains at least one additional heteroatom selected from nitrogen, oxygen, sulfur, or combinations thereof. The heterocyclic group can be saturated or unsaturated. The ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

In some embodiments of the cationic ring structure, the heterocyclic group is fused to a cyclic or bicyclic group that is saturated or unsaturated and that has 0 to 3 heteroatoms. For example, the heterocyclic group can be fused to an aromatic group having 0 to 3 heteroatoms.

Suitable examples of five member heterocyclic groups that contain a positively charged nitrogen atom include, but are not limited to, a pyrazolium ion, imidazolium ion, triazolium ion, isoxazolium ion, oxazolium ion, thiazolium ion, isothiazolium ion, oxadiazolium ion, oxatriazolium ion, dioxazolium ion, and oxathiazolium ion.

Examples of five member heterocyclic groups that have a fused cyclic group include, but are not limited to, an indazolium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, and purinium ion.

Suitable examples of six member heterocyclic groups that contain a positively charged nitrogen atom include, but are not limited to, a pyridazinium ion, pyrimidinium ion, pyrazinium ion, piperazinium ion, triazinium ion, oxazinium ion, oxathiazinium ion, oxadiazinium ion, and morpholinium ion.

Examples of six member heterocyclic groups that have a fused cyclic group include, but are not limited to, cinnolinium ion, quinazolinium ion, benzopyrazinium ion, benzopiperazinium ion, benzotriazinium ion, benzoxazinium ion, benzoxathiazinium ion, benzoxadizinium ion, and benzomorpholinium ion.

Specific examples of arylsulfinate salts having an anion of Formula I and a cation with a nitrogen containing ring structure include, but are not limited to, 1-ethyl-3-methylimidazolium 4-methylbenzenesulfinate, morpholinium 4-cyanobenzenesulfinate, 3-ethyl-2-methylbenxoxazolium 4-cyanobenzenesulfinate, and 1-Methyl-4-aza-1-azoniabicyclo[2.2.2]octane 4-cyanobenzenesulfinate.

In other embodiments of an arylsulfinate salt, the anion is of Formula I

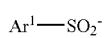

as described above and the cation is of Formula III

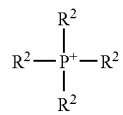

where each $R^2$ is independently an alkyl or aryl that is substituted or unsubstituted. An alkyl can be substituted with a hydroxy. An aryl can be substituted with an alkyl, hydroxy, or combinations thereof.

In some examples of cations according to Formula III, each $R^2$ is an aryl group such as phenyl. The cation can be an unsubstituted or substituted tetraphenylphosphonium ion.

Exemplary arylsulfinates having an anion of Formula I and a cation of Formula III include, but are not limited to, tetraphenylphosphonium 4-cyanobenzenesulfinate.

The arylsulfinate salts typically have a solubility equal to or greater than 0.05, 0.06, 0.07, 0.08, 0.09, or 0.1 moles/liter in a given material such as a solvent or monomer. Thus, the arylsulfinates are not limited to applications that include aqueous formulations or aqueous systems with a large amount (e.g., 30 to 70 weight percent) of a cosolvent such as an alcohol.

The arylsulfinates can be used to polymerize monomers without the need of adding a solvent for the purpose of dissolving the arylsulfinates. For example, the arylsulfinates can be used to polymerize non-polar monomers such as 1,6-hexanediol diacrylate, stearyl acrylate, lauryl acrylate, and the like. The polymerization reaction can occur in the absence of added solvents (i.e., the arylsulfinates are soluble in these non-polar monomers).

In some embodiments, the arylsulfinates can be stored as a neat compound at room temperature without undergoing oxidative degradation. For example, some of the arylsulfinates can be stored for greater than one day, greater than 2 days, greater than 1 week, greater than 2 weeks, or greater than 1 month. The time required at room temperature (i.e., 20° C. to 25° C.) to oxidize 50 percent of the compound ($t_{1/2}$) can be used to compare the relative ease of oxidative degradation of various arylsulfinates. The $t_{1/2}$ is calculated based on pseudo-first order kinetics as described in K. A. Connors, *Chemical Kinetics: The Study of Reaction Rates in Solution*, Chapter 2, VCH, New York, 1990.

The arylsulfinates disclosed herein, at least in some applications, have improved solubility in a variety of monomers, enhanced storage stability, or a combination thereof compared to arylsulfinates having a cation selected, for example, from an alkali metal or alkaline earth metal.

EXAMPLES

Unless otherwise noted, as used herein:

the solvents and reagents were or can be obtained from Aldrich Chemical Co., Milwaukee, Wis. or may be synthesized by known methods;

electrochemical instrumentation for cyclic voltammetry was obtained from Princeton Applied Research, Oak Ridge, Tenn.;

N,N-dimethylformamide was obtained from EM Science, Gibbstown, N.J.;

4-(trifluoromethyl)benzenesulfonyl chloride was obtained from Alfa Aesar, Ward Hill, Mass.;

the term "emim" refers to the 1-ethyl-3-methylimidazolium cation;

the term "4-HBA" refers to 4-hydroxybutyl acrylate;

the term "HEA" refers to 2-hydroxyethyl acrylate;

the term "HDDA" refers to 1,6-hexanediol diacrylate;

the term "EYB" refers to Erythrosin Yellowish blend, which is a mixture of 90% Erythrosin B and 10% Eosin Y and which was obtained from Aldrich Chemical Co.;

the term "Cyanine 1" refers to 3-methyl-2-[5-(3-methyl-2-benzothiazolinylidene)-1,3-pentadienyl]benzothiazolium iodide and was prepared according to the general method disclosed in *Biochemistry*, Vol. 13, no. 42 (1974), pp. 3315-3330

Methods

Measurement of Oxidation Potentials

The electrochemical measurements of the exemplary arylsulfinates were made using an EG&G PARC Model 175 Universal Programmer, interfaced to a Princeton Applied Research Model 173 potentiostat/galvanostat fitted with a Princeton Applied Research Model 179 Digital Coulometer and Model 178 Electrometer. The signal was digitized using a Model DI-151R5 Waveform Recording System (available from DATAQ Instruments, Inc., Akron, Ohio) and then stored and analyzed on a Dell OptiPlex XM 590 pc. The scan rates were 100 mV/sec.

The electrochemical measurements were made using a three-electrode configuration: a reference electrode, a working electrode, and a counter electrode. The reference electrode was a fritted electrode (obtained from Sargent Welch, Buffalo Grove, Ill.) that was filled with 0.01M $AgNO_3$ in acetonitrile and fitted with a silver wire 1 mm in diameter by approximately 19 cm in length. The counter electrode was a platinum wire 1.0 mm in diameter and approximately 16 cm long (overall length) formed into a coil having a coil diameter of approximately 10 mm and a coil length of about 7.5 cm. The working electrode was a glassy carbon electrode, approximately 3.5 mm in diameter (obtained from BAS, Inc., West Lafayette, Ind.). The glassy carbon electrode was polished using first a 3.0 micron aluminum oxide powder/deionized water slurry, then a 0.3 micron alpha alumina powder/deionized water slurry. The polishing powders were obtained from Buehler LTD, Evanston, Ill.

The cell was a 50 mL four neck round bottom flask. Each electrode was sealed in the flask using the appropriately sized rubber septum. The fourth inlet was used to introduce an argon purge to remove oxygen and keep atmospheric moisture out of the cell.

The supporting electrolyte was tetrabutylammonium hexafluorophosphate (TBA $PF_6$) (obtained from Southwestern Analytical Chemicals, Inc., Austin, Tex.). The TBA $PF_6$ was dried overnight in a vacuum oven at 80-90° C. before each experiment. The solvent was N,N-dimethylformamide (DMF), and it was used as received without further purification. The solvent was transferred to the electrochemical cell via syringe under an argon atmosphere to minimize atmospheric moisture uptake.

Electrochemical measurements were made by first preparing a 0.1 molar solution of TBA $PF_6$ in DMF. This solution was added to the cell, which contained a small magnetic stir bar, as argon gas was flowing through the cell. After the reference and counter electrodes were connected to the instrumentation, the working electrode was polished as described above and was then inserted into the cell. A background scan was conducted before the exemplary compounds were added to the cell. Then, approximately 10 mg of the compound was added to the cell and, after it had dissolved, the measurement was made to record the oxidation potential. The potential was determined at the peak current for the oxidation or reduction reaction on the first scan. In this configuration, the oxidation potential of ferrocene in an identical electrolyte solution appeared at +0.1 volts versus the reference electrode.

Measurement of Oxidative Stability

The oxidative stability of the exemplary substituted arylsulfinates was determined by proton nuclear magnetic resonance spectroscopy. Spectra of solutions of the compounds in acetonitrile-$d_3$ were obtained at regular intervals. The resonances of the alkyl groups in the cations were used as an internal standard to assess the oxidation of the anion.

Preparative Example 1

Preparation of 4-Cyanobenzenesulfonyl Chloride

An intimate mixture of 4-carboxybenzenesulfonamide (188 g) and $PCl_5$ (430 g) was made by combining the solids in a resealable plastic bag and manually kneading and shaking the bag. The mixture was transferred to a round bottom flask that was fitted with a magnetic stir bar and a hose adapter that was connected to a source of nitrogen gas. The flask was slowly heated to 60° C. in an oil bath and was held at 60° C. for 5 hours as the mixture was stirred. The hose adapter was then connected to a water aspirator through a trap that was cooled with dry ice, and the temperature of the oil bath was increased to 110° C. while the flask was evacuated and liquid distilled into the trap. When the rate of distillation slowed, the hose adapter was again connected to the nitrogen source and the temperature of the oil bath was raised to 155° C. After an additional 13 hours, the hose adapter was again connected to a water aspirator through a trap and more liquid was distilled. The reaction flask was then allowed to cool to room temperature, during which time the brown product solidified. The crude product was vacuum distilled, using a Kugelrhor distillation apparatus (available from Aldrich Chemical Co., Milwaukee, Wis.) at a temperature of 150° C. and a pressure of 0.07 mmHg, into a collection bulb that was cooled in an ice bath. The solid yellow distillate was washed from the collection bulb with $CH_2Cl_2$ and that solution was concentrated to dryness with a rotary evaporator to afford 167.4 g of product.

Preparative Example 2

Preparation of Potassium 4-Ethoxycarbonylbenzenesulfonate

A mixture of sodium 4-carboxybenzenesulfonate (75 g) in deionized water (1200 mL) was heated to 60° C. until the solid was dissolved. This solution was passed through a column of a strongly acidic ion-exchange resin (available under the trade designation AMBERLITE IR-120(PLUS) from Rohm and Haas Co., Philadelphia, Pa.) that had been acidified by washing sequentially with deionized water, concentrated aqueous HCl and deionized water until the pH of the eluate was approximately 5.5. The column was then charged with the solution of sodium 4-carboxybenzenesulfonate and was then washed with deionized water until a total of 2 L of eluate was collected. The deionized water was removed with a rotary evaporator and the resultant intermediate was dried in a vacuum oven overnight at 50° C.

The intermediate was then dissolved in anhydrous ethanol (1 L) in a round bottom flask fitted with a magnetic stir bar, a condenser and a hose adapter that was attached to a source of nitrogen gas. This solution was stirred and heated overnight in an oil bath at 100° C. An additional 500 mL of ethanol was added to the flask and heating and stirring was continued for an additional 4 hours. The solution was allowed to cool to room temperature and was neutralized with alcoholic KOH to the bromothymol blue endpoint. The product precipitated from the solution and was isolated by vacuum filtration, washed with anhydrous ethanol and dried overnight at room temperature to afford 75.1 g of product.

Preparative Example 3

Preparation of 4-Ethoxycarbonylbenzenesulfonyl Chloride

A round bottom flask, fitted with a magnetic stir bar and a hose adapter connected to a source of nitrogen gas, was charged with a solution of potassium 4-ethoxycarbonylbenzenesulfonate (75.1 g) dissolved in a 3:1 (v/v) mixture of acetonitrile (300 mL) and sulfolane (100 mL). As the solution was stirred, $POCl_3$ (55 mL) was added slowly and the stirring mixture was heated at 75° C. under a nitrogen atmosphere for 3 hours. The heterogeneous reaction mixture was allowed to cool to room temperature and was then concentrated using a rotary evaporator. The flask was then cooled in an ice bath and ice was added to the mixture in the flask. The product crystallized as a white solid and was filtered and washed with cold deionized water. The product was dried under vacuum at room temperature and 3 mmHg for 2 hours to afford 76 g of white solid.

Preparative Example 4

Preparation of 1-Chlorosulfonylanthraquinone

Sodium anthraquinone-1-sulfonate (50.0 g) was combined with $POCl_3$ (31 mL) and a 1:2 (v/v) mixture of sulfolane (100 mL) and acetonitrile (200 mL). The mixture was stirred and heated to 110° C. under a nitrogen atmosphere for 44 hours. The mixture was allowed to cool to room temperature and was then further cooled in a refrigerator. The mixture was filtered and the filtrate was poured onto ice in a beaker and this mixture was stirred for 1 hour. The brown precipitate was filtered, washed with deionized water, dried in air and then further dried overnight in a vacuum oven at 45° C. and less than 1 mmHg pressure to give 12.08 g of the product as a brown solid.

Preparative Examples 5-8

Preparation of Substituted Alkali Metal Benzenesulfinates

Substituted alkali metal benzenesulfinates were prepared by hydrolysis of the substituted benzenesulfonyl chlorides that were obtained commercially or were prepared as described in Preparative Examples 1 and 3. Each substituted benzenesulfonyl chloride was stirred for 3 hours at 75° C. in deionized water, at a concentration of 0.2 g of substituted benzenesulfonyl chloride per milliliter of deionized water, with 2.5 equivalents of $Na_2SO_3$ and 2.5 equivalents of $NaHCO_3$ in a round bottom flask. Each reaction mixture was then allowed to cool to room temperature and was then cooled in a refrigerator to 10° C. Each cold solution was acidified with concentrated sulfuric acid until the pH was less than 1.

Each precipitated solid was extracted into ethyl acetate and then the organic phase was evaporated to dryness using a rotary evaporator to afford the substituted benzenesulfinic acid as a colorless solid. Each of the solid substituted benzenesulfinic acids was dissolved in methanol to give approximately 10 weight percent solutions. Deionized water was then added dropwise to each solution until a precipitate just formed. Sufficient methanol was then added to the solution until all of the solid dissolved. Each aqueous methanol solution was neutralized with a 1M aqueous solution of an alkali metal hydroxide (MOH), as indicated in Table 1, to afford the substituted alkali metal substituted benzenesulfinate salts, which were isolated by removal of the solvent with a rotary evaporator.

TABLE 1

| | Preparative Examples 5-8 | | | |
|---|---|---|---|---|
| Preparative Example | Benzenesulfonyl chloride | Wt. Benzenesulfonyl chloride | MOH | Wt. Benzenesulfinate |
| 5 | 4-Cyano | 11.68 g | NaOH | 9.30 g |
| 6 | 4-Ethoxycarbonyl | 6.46 g | LiOH | 3.17 g |
| 7 | 4-Chloro | 5.11 g | LiOH | 3.06 g |
| 8 | 4-Trifluoromethyl | 6.20 g | NaOH | 4.15 g |

Preparative Example 9

Preparation of N,N-Dimethylmorpholinium Hydroxide

To a stirred solution of N-methylmorpholine (10.0 g) in 1,2-dichloroethane (125 mL) at room temperature there was added methyl iodide (14.1 g). The colorless precipitate that formed was filtered and was washed sequentially with 1,2-dichloroethane and petroleum ether. The solid was dried in air at room temperature to afford 21.3 g of product. A sample of this product (1.0 g) was dissolved in deionized water (2 mL) and was passed through a column of strongly basic ion-exchange resin (available under the trade designation DOWEX 1X2-100 from Dow Chemical Co., Midland, Mich.) that had been washed sequentially with 10 g of a 10% aqueous solution of NaOH and 200 mL of deionized water. The sample was washed from the column with 25 mL of deionized water. The eluted solution was concentrated to dryness using a rotary evaporator and was further dried using a vacuum oven at 50° C. overnight to give the product as a colorless solid.

Preparative Example 10

Preparation of 1-Methyl-4-aza-1-azoniabicyclo[2.2.2]octane Hydroxide

To a stirred solution of 1,4-diazabicyclo[2.2.2]octane (10.0 g) in 1,2-dichloroethane (100 mL) at room temperature there was added methyl iodide (12.7 g). The colorless precipitate that formed was filtered and was washed sequentially with 1,2-dichloroethane and petroleum ether. The solid was dried in air at room temperature to afford 21.3 g of product. All of this product was then dissolved in deionized water (200 mL) and was stirred at room temperature while ammonium hexafluorophosphate (13.7 g) was slowly added to the solution. The colorless precipitate that formed was vacuum filtered and was washed with a small amount of deionized water. The solid was allowed to dry in air at room temperature overnight and was further dried using a vacuum oven at 60° C. overnight to afford 7.1 g of product. A sample of this product (1.0 g) was dissolved in deionized water (2 mL) and was passed through a column of strongly basic ion-exchange resin (available under the trade designation DOWEX 1X2-100 from Dow Chemical Co., Midland, Mich.) that had been washed sequentially with 10 g of a 10% aqueous solution of NaOH and 200 mL of deionized water. The sample was washed from the column with 25 mL of deionized water. The eluted solution was concentrated to dryness using a rotary evaporator and was further dried using a vacuum oven at 50° C. overnight to give the product as a colorless solid.

Preparative Example 11

Preparation of 3-Ethyl-2-methylbenzoxazolium Chloride

A solution of 3-ethyl-2-methylbenzoxazolium iodide (1.0 g) in deionized water (20 mL) was passed through a column of ion-exchange resin (available under the trade designation DOWEX 1X2-100 from Dow Chemical Co., Midland, Mich.) that had been washed sequentially with deionized water (200 mL), saturated aqueous NaCl (50 mL), and deionized water (200 mL). The product was washed from the column with approximately 50 mL of deionized water and was concentrated to dryness using a rotary evaporator to afford 0.73 g of product.

Examples 1-4

Preparation of Substituted Tetrabutylammonium Benzenesulfinates

Substituted tetrabutylammonium benzenesulfinates were prepared from the corresponding alkali metal sulfinates. Each alkali metal sulfinate was dissolved in deionized water to give a 0.1M solution that was acidified with concentrated sulfuric acid to afford the sulfinic acid as a colorless precipitate. Each mixture was extracted with ethyl acetate and then the organic phase was evaporated to dryness using a rotary evaporator. Each resultant solid was dissolved in 50% (v/v) aqueous methanol and this solution was titrated with an aqueous solution of tetrabutylammonium hydroxide. Each mixture was evaporated to dryness using a rotary evaporator to afford the product as a yellow oil. The $^1$H and $^{13}$C NMR spectra of each compound were consistent with the assigned structure. Details of these preparations and oxidation and stability data are given in Table 2.

TABLE 2

| | Examples 1-4 | | | |
| --- | --- | --- | --- | --- |
| | Example | | | |
| | 1 | 2 | 3 | 4 |
| Alkali Metal Benzenesulfinate | 4-Chloro | 4-Ethoxycarbonyl | 4-Trifluoromethyl | 4-Cyano |
| Wt. Alkali Metal Benzenesulfinate | 0.50 g | 0.58 g | 1.72 g | 2.00 g |
| Wt. Tetrabuylammonium Benzenesulfinate | 0.98 g | 1.27 g | 3.51 g | 4.18 g |
| $E_{ox}$ | 0.09 V | 0.11 V | 0.18 V | 0.15 V |
| $t_{1/2}$ (days) | 138 | 174 | 88 | >300 |

Example 5

Preparation of emim 4-Methylbenzenesulfinate

A mixture of sodium 4-methylbenzenesulfinate (3.1 g) and anhydrous ethanol (80 mL) in a round bottom flask, fitted with a magnetic stir bar, was heated to approximately 75° C. with stirring. The mixture was allowed to cool to approximately 40° C. and then a solution of 1-ethyl-3-methylimidazolium chloride (2.0 g) in anhydrous ethanol (20 mL) was added to the flask. The mixture was stirred for 2 hours after which time it was filtered. The filtrate was concentrated to dryness using a rotary evaporator to give a heterogeneous yellow oil which was taken up in $CHCl_3$. This mixture was filtered and then the filtrate was concentrated to dryness using a rotary evaporator to afford 3.12 g of the product as a yellow oil.

Example 6

Preparation of Tetraphenylphosphonium 4-Cyanobenzenesulfinate

A solution of sodium 4-cyanobenzenesulfinate (1.0 g) in anhydrous ethanol (100 mL) was prepared in a 250 mL Erlenmeyer flask by heating the solution to boiling on a hot plate with magnetic stirring. To the boiling solution was added a hot solution of tetraphenylphosphonium chloride (1.98 g) in anhydrous ethanol (50 mL) with constant stirring. The stirring solution was allowed to cool for 30 minutes, during which time a colorless precipitate appeared. The flask was then cooled in an ice-bath for an additional 30 minutes with stirring. The mixture was vacuum filtered and the filtrate was dried using a rotary evaporator to yield a deep yellow oil that contained some solid material. This residue was dissolved in chloroform (50 mL) and the mixture was stirred for 20 minutes and was then vacuum filtered. The deep yellow solution was concentrated to dryness using a rotary evaporator to afford a clear yellow oil that was further dried under vacuum for 1 hour at 3 mmHg to yield 2.20 g of the product as a bright yellow wax.

Example 7

Preparation of Tetrabutylammonium 1-Anthraquinone Sulfinate

A solution of 1-chlorosulfonylanthraquinone (12.05 g) was combined with deionized water (200 mL), $Na_2SO_3$ (18.34 g) and $NaHCO_3$ (12.22 g) in a round bottom flask. The mixture was stirred and heated under a nitrogen atmosphere at 65° C. for 2 hours. The solution was then allowed to cool to room temperature and was then further cooled in a refrigerator. The precipitated solid that formed was isolated by filtration and was allowed to dry in air. The solid was transferred to a flask to which was added 200 mL of a 2:1 (v/v) mixture of methanol and deionized water. The solution was titrated with 40% aqueous tetrabutylammonium hydroxide until a deep red color persisted. The solvent was removed with a rotary evaporator and the deep red oil was dried under high vacuum for 2 days at 45° C. to afford 16.98 g of product.

Example 8

Preparation of Tetrabutylammonium 1-Naphthalene Sulfinate

A round bottom flask was charged with 1-naphthalenesulfonyl chloride (20.0 g), $Na_2SO_3$ (33.36 g), $NaHCO_3$ (22.24 g) and deionized water (350 mL). The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$ which resulted in the formation of a precipitate. The mixture was extracted three times with 100 mL of ethyl acetate. The organic extracts were combined and the solvent was removed with a rotary evaporator to give a colorless solid that was then dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 36.4 g of a yellow waxy solid.

Example 9

Preparation of Tetrabutylammonium 2-Naphthalene Sulfinate

A round bottom flask was charged with 2-naphthalenesulfonyl chloride (24.73 g), $Na_2SO_3$ (41.25 g), $NaHCO_3$ (41.25 g) and 350 mL deionized water. The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$, which resulted in the formation of a precipitate.

The mixture was extracted three times with 100 mL of ethyl acetate. The organic extracts were combined and the solvent was removed with a rotary evaporator to give a colorless solid that was then dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 46.9 g of a yellow waxy solid.

Example 10

Preparation of N,N-Dimethylmorpholinium 4-Cyanobenzenesulfinate

Concentrated sulfuric acid was slowly added to a solution of sodium 4-cyanobenzenesulfinate (0.15 g) in deionized water (10 mL). A precipitate formed and sulfuric acid was added dropwise until it appeared that no more precipitate was forming. The mixture was extracted twice with ethyl acetate (20 mL) and the combined organic phases were concentrated to dryness using a rotary evaporator. The resultant solid was dissolved in 50 weight percent aqueous methanol and this solution was titrated with a solution of N,N-dimethylmorpholinium hydroxide (0.85 g) in deionized water (5 mL). The solution was concentrated to dryness using a rotary evaporator and was further dried using a vacuum oven at room temperature overnight. The resultant solid was then dissolved in deionized water and this solution was extracted twice with ethyl acetate (20 mL). The combined organic phases were concentrated to dryness using a rotary evaporator. The resultant solid was further dried using a vacuum oven overnight at room temperature to afford 0.24 g of product as a yellow oil.

Example 11

Preparation of 1-Methyl-4-aza-1-azoniabicyclo[2.2.2]octane 4-Cyanobenzenesulfinate Concentrated sulfuric acid was slowly added to a solution of sodium 4-cyanobenzenesulfinate (0.25 g) in deionized water (10 mL). A precipitate formed and sulfuric acid was added dropwise until it appeared that no more precipitate was forming. The mixture was extracted twice with ethyl acetate (20 mL) and the combined organic phases were concentrated to dryness using a rotary evaporator. The resultant solid was dissolved in 50 weight percent aqueous methanol and this solution was titrated with a solution of the product of Preparative Example 10 (0.27 g) in deionized water (5 mL) to a pH of approximately 7.2. The solution was concentrated to dryness using a rotary evaporator and was further dried using a vacuum oven at room temperature overnight to afford 0.45 g of product as a yellow waxy solid.

Example 12

Preparation of N-Hexadecylpyridinium 4-Cyanobenzenesulfinate

A solution of N-hexadecylpyridinium chloride (1.6 g) in ethanol (20 mL) was added to an Erlenmeyer flask containing a magnetically stirred boiling solution of sodium 4-cyanobenzenesulfinate (1.0 g) in anhydrous ethanol (200 mL). The mixture was allowed to cool to room temperature and was then further cooled in an ice bath. The mixture was filtered and the filtrate was concentrated to dryness using a rotary evaporator. The residue was then dissolved in chloroform (100 mL), filtered, and concentrated to dryness using a rotary evaporator to afford 2.4 g of product.

Example 13

Preparation of 3-Ethyl-2-methylbenzoxazolium 4-Cyanobenzenesulfinate

A solution of 3-ethyl-2-methylbenzoxazolium chloride (0.73 g) in ethanol (20 mL) was added to an Erlenmeyer flask containing a magnetically stirred boiling solution of sodium 4-cyanobenzenesulfinate (0.1 g) in anhydrous ethanol (20 mL). The mixture was allowed to cool to room temperature and was then further cooled in an ice bath. The mixture was filtered and the filtrate was concentrated to dryness using a rotary evaporator. The residue was mixed with deionized water and this mixture was extracted with ethyl acetate (2×20 mL). The combined organic extracts were concentrated to dryness using a rotary evaporator. The resultant solid was then dissolved in methylene chloride, filtered and evaporated to dryness using a rotary evaporator to afford 0.08 g of product.

Examples 14-17

Photocuring of HEA Using Tetrabutylammonium 4-Cyanobenzenesulfinate

A stock solution of HEA and 1 weight percent tetrabutylammonium 4-cyanobenzenesulfinate was prepared. Screw-cap vials were charged with approximately 1 g of this solution. An amount of a dye was added to each vial to give a dye concentration sufficient to provide a lightly colored solution, typically between 50 and 1000 ppm, depending on the dye. Each solution was purged with nitrogen gas for 30 seconds after which time the vials were sealed. Each solution was irradiated with a 100 W quartz-tungsten-halogen (QTH) light source (model I-100, available Cuda Fiberoptics, Jacksonville, Fla.) by holding and slowly agitating each vial approximately 2 cm in front of the light source. The light source shutter was fully open. Cure time was considered to be the time that it took for the solution to no longer flow in the vial as the vial was agitated. The results are given in Table 3.

TABLE 3

Examples 14-17

| Example | Dye | Cure Time (sec) |
|---|---|---|
| 14 | Methylene blue | 12 |
| 15 | Basic Blue 3 | 28 |
| 16 | Cyanine 1 | 150 |
| 17 | Rose Bengal | 360 |

Example 18

Photocuring of 4-HBA Using Tetrabutylammonium 4-Cyanobenzenesulfinate and Methylene Green A mixture of 4-HBA (0.5 g) with 1 weight percent of the product of Example 4 was prepared. Methylene green was added in an amount sufficient to provide a lightly colored solution. The sample was evaluated for rate and extent of cure by photo differential scanning calorimetry (photo-DSC) using a model DSC2920 calorimeter (available from TA Instruments, New Castle, Del.) with actinic radiation lower in energy than 300 nm at an irradiance of 20 mW/cm$^2$. The results are given in Table 4.

TABLE 4

Curing of Examples 18

| Example | Initial Slope (W/g-min) | Time to peak maximum (min) | Total evolved heat (J/g) |
|---|---|---|---|
| 18 | 26 | 0.14 | 380 |

Examples 19-22

Photocuring of HDDA Using Tetrabutylammonium Arylsufinate Salts and EYB

A mixture of HDDA (11.03 g) and EYB (0.056 g) in a glass vial was sonicated for five minutes using a laboratory sonication bath that was filled with water. The mixture was then filtered using 0.45 micron syringe filter to give a pink solution which was then divided into nine weighed portions in separate screw cap glass vials. To each of four of the vials was added one of the tetrabutylammonium arylsulfinate salts from Examples 2, 4, 8, and 9 in a quantity sufficient to give a 1 weight percent mixture of the tetrabutylammonium arylsulfinate salt in the HDDA solution. Each of these vials was sonicated for five minutes in a sonication bath and then each mixture was purged with nitrogen gas for two minutes, after which time the vials were sealed. Each mixture was irradiated with a 100 W quartz-tungsten-halogen (QTH) light source (model I-100, available Cuda Fiberoptics, Jacksonville, Fla.) by holding and slowly agitating each vial approximately 2 cm in front of the light source. The light source shutter was fully open. Cure time was considered to be the time that it took for the solution to no longer flow in the vial as the vial was agitated. The results are given in Table 5.

TABLE 5

Curing of Examples 19-22

| Example | Arylsulfinate salt from Example | Cure Time (sec) |
|---|---|---|
| 19 | 2 | 30 |
| 20 | 4 | 22 |
| 21 | 8 | 7 |
| 22 | 9 | 5 |

Comparative Examples 1-4

Irradiation of HDDA Using Alkali Metal Benzenesulfinate Salts and EYB

To each of four of the remaining vials containing HDDA and EYB from Examples 19-22 was added one alkali metal benzenesulfinate salt, as indicated in Table 6, in a quantity sufficient to give a 1 weight percent mixture of the alkali metal arylsulfinate salt in the HDDA solution. Each of these vials was sonicated for five minutes in a sonication bath and then each mixture was purged with nitrogen gas for two minutes, after which time the vials were sealed. Each mixture was irradiated with a 100 W quartz-tungsten-halogen (QTH) light source (model I-100, available Cuda Fiberoptics, Jacksonville, Fla.) by holding and slowly agitating each vial approximately 2 cm in front of the light source. The light source shutter was fully open. Each vial was irradiated for 90 seconds, after which time each of the mixtures was observed not to be cured.

TABLE 6

Substituted alkali metal benzenesulfinate salts

| Comparative Example | Substituted alkali metal benzenesulfinate salt |
|---|---|
| 1 | Lithium 4-(trifluoromethyl)benzenesulfinate |
| 2 | Lithium 4-chlorobenzenesulfinate |
| 3 | Sodium 4-cyanobenzenesulfinate |
| 4 | Lithium 4-carboethoxybenzenesulfinate |

Comparative Example 5

Irradiation of a mixture of HDDA and EYB

The HDDA and EYB mixture in the remaining vial from Examples 19-22 was purged with nitrogen gas for two minutes, after which time the vial was sealed. The mixture was irradiated with a 100 W quartz-tungsten-halogen (QTH) light source (model I-100, available Cuda Fiberoptics, Jacksonville, Fla.) by holding and slowly agitating the vial approximately 2 cm in front of the light source. The light source shutter was fully open. The vial was irradiated for 90 seconds, after which time the mixture was observed not to be cured.

We claim:

1. An arylsulfinate salt comprising:
an anion of Formula I

   I wherein $Ar^1$ is a substituted phenyl, an unsubstituted or substituted $C_{7\text{-}30}$ aryl, or an unsubstituted or substituted $C_{3\text{-}30}$ heteroaryl, said substituted $Ar^1$ having a substituent that is an electron withdrawing group or an electron withdrawing group in combination with an electron donating group; and
a cation comprising a ring structure comprising a 4 to 12 member heterocyclic group with a positively charged nitrogen atom and at least one other heteroatom selected from nitrogen, oxygen, sulfur, or combinations thereof, said heterocyclic group being saturated or unsaturated, wherein said ring structure can be unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, or halocarbonyl group.

2. The arylsulfinate salt of claim 1, wherein said heterocyclic group is fused to a cyclic or bicyclic group that is saturated or unsaturated and that has 0 to 3 heteroatoms.

3. The arylsulfinate salt of claim 1, wherein the heterocyclic group is a heterobicyclic group.

4. The arylsulfinate salt of claim 1, wherein the heterocyclic group is selected from a pyrazolium ion, imidazolium ion, triazolium ion, isoxazolium ion, oxazolium ion, thiazolium ion, isothiazolium ion, oxadiazolium ion, oxatriazolium ion, dioxazolium ion, oxathiazolium ion, pyridazinium ion, pyrimidinium ion, pyrazinium ion, piperazinium ion, triazinium ion, oxazinium ion, oxathiazinium ion, oxadiazinium ion, or morpholinium ion.

5. The arylsulfinate salt of claim 1, wherein the heterocyclic group is selected from an indazolium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, purinium ion, cinnolinium ion, quinazolinium ion, benzopyrazinium ion, benzopiperazinium ion, benzotriazinium ion, benzoxazinium ion, benzoxathiazinium ion, benzoxadizinium ion, or benzomorpholinium ion.

6. The arylsulfinate salt of claim 1, wherein the $Ar^1$ group of the arylsulfinate salt is a substituted phenyl, an unsubstituted or substituted naphthyl, or an unsubstituted or substituted anthraquinonyl, said substituted $Ar^1$ having a substituent that is an electron withdrawing group or an electron withdrawing group in combination with an electron donating group.

7. The arylsulfinate salt of claim 1, wherein the anion of the arylsulfinate salt is a benzenesulfinate substituted with an electron withdrawing group electron selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

8. The arylsulfinate salt of claim 1, wherein the arylsulfinate salt is N,N-dimethylmorpholinium 4-cyanobenzenesulfinate, 1-methyl-4-aza-1-azoniabicyclo [2.2.2]octane 4-cyanobenzenesulfinate, 3-ethyl-2-methylbenzoxazolium 4-cyanobenzenesulfinate, N-hexadecylpyridinium 4-cyanobenzenesulfinate, or combinations thereof.

9. An arylsulfinate salt comprising:
an anion of Formula I

   I wherein $Ar^1$ is a substituted phenyl, a substituted $C_{7\text{-}30}$ aryl, or an unsubstituted or substituted $C_{3\text{-}30}$ heteroaryl, said substituted $Ar^1$ having a substituent that is an electron withdrawing group or an electron withdrawing group in combination with an electron donating group, wherein the electron withdrawing group electron is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof and
a cation is of Formula III

   III where each $R^2$ is independently an unsubstituted alkyl, an alkyl substituted with a hydroxy, an unsubstituted aryl, or an aryl substituted with an alkyl, hydroxy, or combinations thereof.

10. The arylsulfinate salt of claim 9, wherein the compound is tetraphenylphosphonium 4-cyanobenzenesulfinate.

11. The arylsulfinate salt of claim 9, wherein the $Ar^1$ group of the arylsulfinate salt is a substituted phenyl, a substituted naphthyl, or an unsubstituted or substituted anthraquinonyl, said substituted $Ar^1$ having a substituent that is an electron withdrawing group or an electron withdrawing group in combination with an electron donating group.

12. The arylsulfinate salt of claim 9, wherein the anion of Formula I is 4-cyanobenzenesulfinate.

13. The arylsulfinate salt of claim 9, wherein the anion of Formula I is 4-ethoxycarbonylbenzenesulfinate.

14. An arylsulfinate salt comprising:
a cation is of Formula III an anion of Formula I

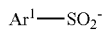

I wherein $Ar^1$ is a substituted phenyl, a substituted $C_{7-30}$ aryl, or a substituted $C_{3-30}$ heteroaryl, said substituted $Ar^1$ having a substituent that is an electron withdrawing group in combination with an electron donating group, wherein the electron withdrawing group electron is selected from halo, fluoroalkyl, perfluoroalkyl, or combinations thereof and wherein the electron donating group is selected from a primary amino, secondary amino, tertiary amino, hydroxy, alkoxy, aryloxyl, or combinations thereof and

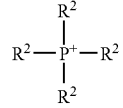

III where each $R^2$ is independently an unsubstituted alkyl, an alkyl substituted with a hydroxy, an unsubstituted aryl, or an aryl substituted with an alkyl, hydroxy, or combinations thereof.

* * * * *

UNITED STATES PATENT AND TRADEMARK OFFICE
CERTIFICATE OF CORRECTION

PATENT NO. : 7,732,633 B2
APPLICATION NO. : 12/428634
DATED : June 8, 2010
INVENTOR(S) : Rajdeep S Kalgutkar et al.

It is certified that error appears in the above-identified patent and that said Letters Patent is hereby corrected as shown below:

Column 5
Line 36; Delete "a" and insert -- an --, therefor.

Column 9
Line 29; Delete "thereof," and insert -- thereof; --, therefor.

Column 10
Line 37; Delete "naphtyridinium" and insert -- naphthyridinium --, therefor.

Column 11
Line 40; Delete "tetraalkyammonium" and insert -- tetraalkylammonium --, therefor.

Column 12
Line 15; Delete "benzopyrilium" and insert -- benzopyrylium --, therefor.
Line 23; Delete "fluorosceins," and insert -- fluoresceins, --, therefor.

Column 19
Line 13; After "3330" insert -- . --.

Column 20
Line 39; Delete "Kugelrhor" and insert -- Kugelrohr --, therefor.

Column 24 (Table 2)
Line 18-19; Delete "Tetrabuylammonium" and insert -- Tetrabutylammonium --, therefor.

Column 28
Line 14; Delete "Arylsufinate" and insert -- Arylsulfinate --, therefor.

Signed and Sealed this
Thirtieth Day of August, 2011

David J. Kappos
*Director of the United States Patent and Trademark Office*

CERTIFICATE OF CORRECTION (continued)
U.S. Pat. No. 7,732,633 B2

Column 30
Line 43; Claim 9 , delete "thereof and" and insert -- thereof; and --, therefor.

Column 31
Line 18; Claim 14, delete "thereof and" and insert -- thereof; and --, therefor.